United States Patent [19]

Hardt

[11] Patent Number: 4,657,106

[45] Date of Patent: Apr. 14, 1987

[54] "EAR" HEARING AID

[75] Inventor: Heinz Hardt, Vienna, Austria

[73] Assignee: Viennatone Gesellschaft m.b.H., Vienna, Austria

[21] Appl. No.: 795,203

[22] Filed: Nov. 5, 1985

[30] Foreign Application Priority Data

Nov. 26, 1984 [AT] Austria ................................ 3747/84

[51] Int. Cl.[4] ................................................ A61B 7/02

[52] U.S. Cl. .................................... 381/68.4; 181/130; 181/135; 381/68.6

[58] Field of Search ................................ 181/130, 135; 179/107 E; 381/69; 220/224, 254

[56] References Cited

U.S. PATENT DOCUMENTS 2,325,590 8/1943 Carlisle et al. .................. 179/107 E
3,047,089 7/1962 Zwislocki ............................ 181/135
3,345,737 10/1967 Gordon ....................... 179/107 E X
3,598,928 8/1971 Hickox ............................ 179/107 E
3,964,609 6/1976 Perrella .......................... 220/254 X
4,303,173 12/1981 Nergard ............................. 220/254
4,471,490 9/1984 Bellagiore ................... 179/107 E X
4,584,437 4/1986 Giannetti .......................... 381/69 X

*Primary Examiner*—Benjamin R. Fuller
*Attorney, Agent, or Firm*—Kurt Kelman

[57] ABSTRACT

A hearing aid adapted to be worn in the ear, comprises a housing receiving a sound transducer and a sound amplifier, the housing being shaped to fit into the ear and having an upper rim, a mounting plate defining a space for holding a battery and a sound volume adjustment control, the mounting plate having a circumferentially extending outer rim, and detachable fastening means connecting the upper housing rim and the outer mounting plate rim.

9 Claims, 11 Drawing Figures

"EAR" HEARING AID

Figure 1:
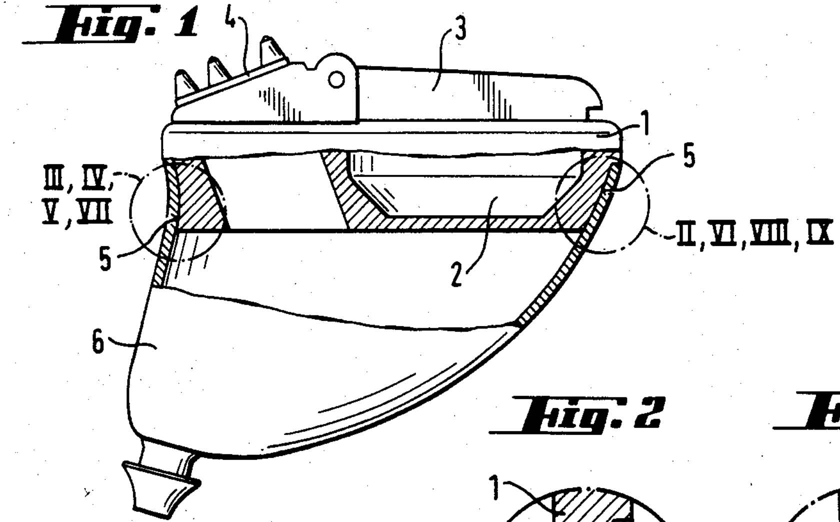

The present invention relates to a hearing aid adapted to be worn in the ear, which comprises a housing receiving a sound transducer and a sound amplifier, the housing being shaped to fit into the ear, and a mounting plate placed on the housing and detachably connected thereto, the mounting plate defining a space for holding a battery and a sound volume adjustment control.

Modular "In the Ear" hearing aids, which are worn in the concha and extend to the auditory canal area or into the ear canal, are known and conventionally comprise essentially a mounting plate and a housing designed to fit the concha or outer ear, which housing may be of standard size and shape or may be individually molded from an impression taken of the ear of an individual. The mounting plate defines a space for holding a battery and a cover for this space as well as a sound volume adjustment control with an on/off switch. The sound transducer, i.e. a microphone, and a sound amplifier are usually affixed to the underside of the mounting plate. When the hearing aid is assembled, the sound receiver is usually first mounted in the housing and the mounting plate with the above-indicated assembled structures is then bonded as cover to the open housing. In the case of individually molded hearing aid housings, the mounting plate has a larger diameter than the largest diameter of the individually molded housings to be expected. After this out-sized mounting plate has been bonded to the housing, the circumference of the mounting plate is milled to fit the size of the housing to which it has been bonded. In the case of standard-sized housings, the mounting plate may be shaped to fit the housing so that no milling is required after the two parts are bonded together.

In either case, the mounting plate and the housing are bonded together, regardless of whether the housing is made of metal or of a suitable synthetic resin, such as an acrylic resin. However, bonding the two hearing aid parts together with an adhesive has the disadvantage that opening of the housing for repairs or other reasons is very difficult. Breaking the adhesive bond requires much skill and experience if a total destruction of the instrument is to be avoided.

For the above reason, it has been proposed to connect the mounting plate and the housing detachably. For example, published European patent application No. 2 85 032 discloses an arrangement in which two screws are passed perpendicularly through the mounting plate into threads affixed to the interior of the hearing aid housing whereby the mounting plate and the housing are detachably fastened to each other. However, this arrangement has the disadvantage that the threads in the housing interior take up relatively much space, which is lost for accommodating the required hearing aid components. Furthermore, accurate positioning of the screw threads is difficult.

It was, therefore, attempted to provide a mounting plate consisting of two concentric parts. The inner part is as small as possible to receive the battery, sound volume adjustment control, amplifier, etc. and this small part is snapped into the surrounding outer part. The hearing aid is assembled by bonding the outer annular mounting plate part to the housing to attach it adhesively thereto, after which this part may be milled to provide a suitable fit, and the inner mounting plate part carrying the hearing aid components is then snapped into the outer part. The main disadvantage of this arrangement resides in the fact that the inner mounting plate part cannot be made smaller than in conventional hearing aids in which the mounting plate carries various components thereof and the outer mounting plate ring serving to affix the mounting plate to the housing detachably takes up additional space. Therefore, this arrangement is not advantageous for small hearing aids designed to be worn in the concha.

It is the primary object of this invention to avoid the indicated disadvantages in miniature hearing aids. The invention accomplishes this result in a hearing aid of the first-described type with a housing having an upper rim, a mounting plate having a circumferentially extending outer rim, and detachable fastening means, such as screws, connecting the upper housing rim and the outer mounting plate rim.

This manner of detachably fastening the hearing aid housing to the mounting plate is particularly useful for standardized housings having a predetermined shape and size since there is no difficulty in providing injection-molded synthetic resin mounting plates with circumferentially extending outer rims exactly fitting such housings.

Figure 8:
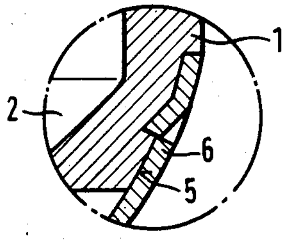
Figure 9:
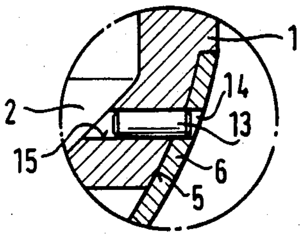
Figure 10:
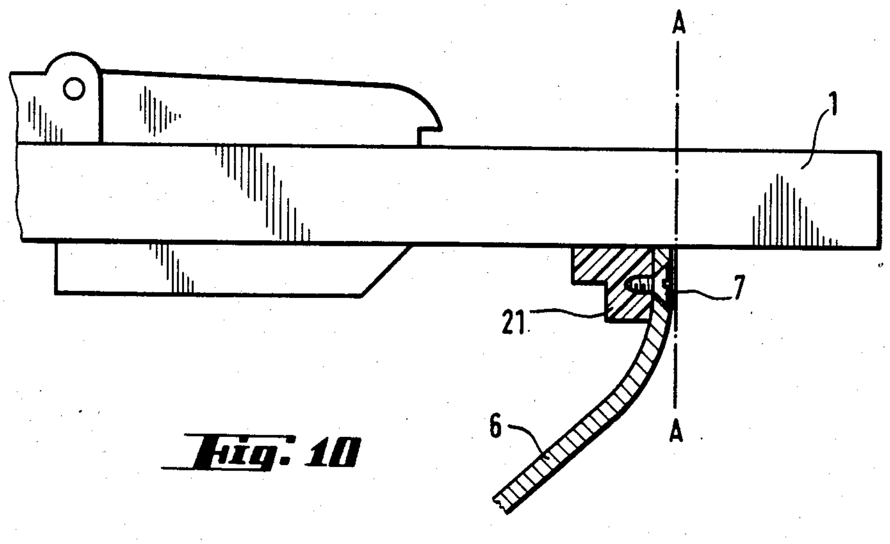
Figure 11:
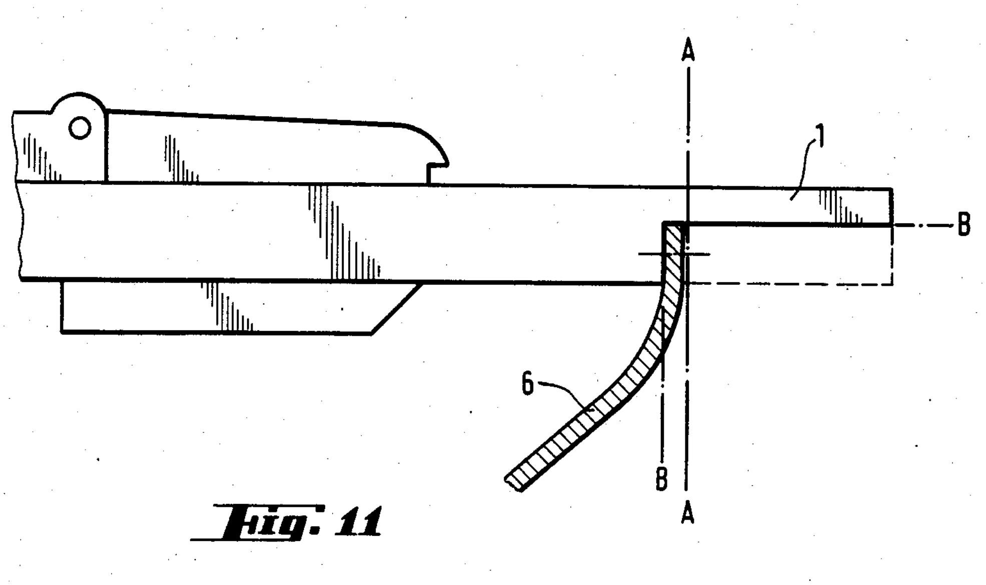

The above and other objects, advantages and features of the invention will become more apparent from the following detailed description of certain now preferred embodiments thereof, taken in conjunction with the accompanying drawing wherein FIG. 1 is a side elevational view, partly in section, of a hearing aid according to the present invention;

FIGS. 2 to 9 are fragmentary sectional views showing different embodiments of the detachable fastening means; and FIGS. 10 and 11 are fragmentary side elevational views, partly in section, of two further embodiments of this invention.

Referring now to the drawing wherein like reference numerals designate like parts functioning in a like manner in all figures, there is shown a hearing aid adapted to be worn in the ear, which comprises housing 6 receiving a sound transducer, i.e. a microphone, and a sound amplifier in a conventional manner (not shown). The housing is shaped to fit into the ear and has an upper rim. In a manner well known per se, the hearing aid further comprises mounting plate 1 defining space 2 for holding a battery and sound volume adjustment control 4, battery cover 3 being mounted over battery space 2. The underside of the mounting plate has circumferentially extending outer rim 5 which, in the range of battery space 2, forms a wall of the battery space. Outer mounting plate rim 5 fits more or less accurately into the upper opening of housing 6 so that the mounting plate sits in this upper housing opening in the manner well shown in FIG. 1. The location of the detachable fastening between the mounting plate and the housing is shown by the dash-dotted circles in this figure, the Roman numerals indicating the embodiments illustrated in the corresponding figures.

Figure 2:
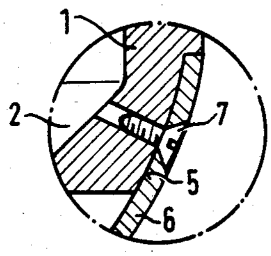
Figure 3:
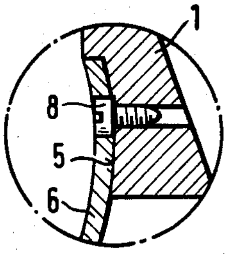

The detachable fastening means connecting the upper housing rim and outer mounting plate rim 5 may be screws, as shown in FIGS. 2 and 3. For this purpose, at least two screws uniformly distributed about the circumference may be used. As illustrated in FIG. 2, countersunk screw 7 is inserted into a corresponding dovetailed hole in the upper housing rim and circumferentially extending outer mounting plate rim 5 defines a threaded bore receiving screw 7. In the modification of FIG. 3, screw 8 with a cylindrical head is used as the detachable fastening means.

Figure 4:
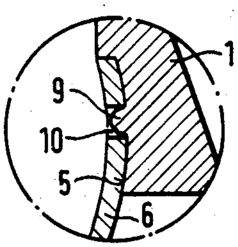

Another embodiment of detachable fastening means particularly useful for thin-walled hearing aid housings, such as housings produced by galvanic precipitation of silver, is shown in FIG. 4. This fastening means comprises a snap connection, the snap connection comprising detent 9 on outer mounting plate rim 5 and the detent fitting into a matching depression constituted by slit 10 in the upper housing rim. Such slits may be readily stamped into metal hearing aid housings.

Figure 5:
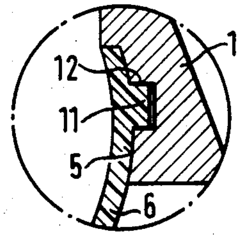
Figure 6:
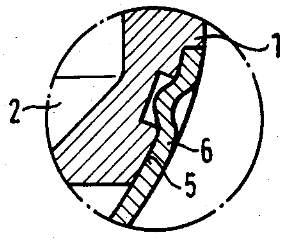
Figure 7:
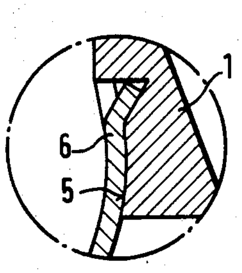

The embodiment of FIG. 5 is particularly useful for relatively thick-walled synthetic resin hearing aid housings. As shown, this snap connection fastening means comprises detent 11 in the upper housing rim and the detent fits into matching depression 12 in outer mounting plate rim 5. Depressions 12 may be provided by suitable molds in which mounting plate 1 is injection-molded or they may be subsequently milled into the mounting plate. If the hearing aid housing is of metal, a suitable bead may be stamped into the upper rim of the metal housing, as shown in FIG. 6, to provide the desired detent. Alternatively, as illustrated in FIGS. 7 and 8, a portion of the upper housing rim may simply be bent to snap-fit into a depression in mounting plate rim 5.

Another embodiment of detachable fastening means is shown in FIG. 9. This comprises pins 13, for example of stainless steel, insertable into aligned bores 14, 15 in the upper housing rim and the outer mounting plate rim. The housing and mounting plate may be detached simply by pushing pins 13 from the outside inwardly, for example by inserting a thin rod or needle into bore 14.

If the detachable fastening means of the invention is to be used in connection with hearing aid housings produced individually from impressions made of the wearer's ears, it cannot be assumed that the mounting plate will fit into the usually somewhat larger upper opening of the custom-made housing. In this case, the outer mounting plate rim may be comprised of at least two bars affixed to the mounting plate, for example by bonding the bars, for example angle brackets, to the underside of the mounting plate. Alternatively, if the mounting plate is thick enough, the outer mounting plate rim is produced by milling off the mounting plate to produce a proper fit of the mounting plate rim with the upper housing rim. Such embodiments are shown in the fragmentary views of FIGS. 10 and 11.

As shown in FIG. 10, angle bracket 21 of synthetic resin is bonded by a suitable adhesive to the underside of mounting plate 1 whose diameter usually exceeds that of the upper rim of custom-made hearing aid housing 6. The location of the angle brackets is so selected that the brackets will fit into the upper housing rim in the illustrated manner, whereupon the mounting plate and housing are detachably fastened to each other in the manner shown in FIG. 2 and described hereinabove.

Afterwards, the mounting plate is milled along line A—A so that its periphery will coincide with that of the housing.

In the embodiment of FIG. 11, which is applicable to relatively thick mounting plates, the circumferentially extending rim of mounting plate 1 fitting the upper rim of housing 6 is produced by milling off a portion of the mounting plate indicated by broken lines, along line B—B. This produces a mounting plate rim which may be detachably fastened to the upper housing rim in any manner hereinabove described.

What is claimed is:

1. A hearing aid adapted to be worn in the ear, which comprises (a) a housing receiving a sound transducer and a sound amplifier, the housing being shaped to fit into the ear and having a circumferentially extending upper rim defining an opening, (b) a mounting plate defining a space for holding a battery and a sound volume adjustment control, the mounting plate having a circumferentially extending outer rim projecting from the mounting plate into the housing opening and insertable therein, the upper housing rim and the outer mounting plate rim engaging along the entire circumference thereof, and (c) detachable fastening means connecting the upper housing rim and the outer mounting plate rim along their entire circumference and fastening the upper housing rim under radially extending fastening force to the outer mounting plate rim.

2. The hearing aid of claim 1, wherein the fastening means comprises radially extending screws.

3. The hearing aid of claim 1, wherein the fastening means comprises a snap connection, the snap connection comprising a radially extending detent on the outer mounting plate rim and the detent fitting into a matching depression in the upper housing rim.

4. The hearing aid of claim 1, wherein the fastening means comprises a snap connection, the snap connection comprising a radially extending detent in the upper housing rim and the detent fitting into a matching depression in the outer mounting plate rim.

5. The hearing aid of claim 1, wherein the fastening means comprises radially extending pins insertable into aligned bores in the upper housing rim and the outer mounting plate rim.

6. The hearing aid of claim 1, wherein the outer mounting plate rim is comprised of at least two bars affixed to the mounting plate.

7. The hearing aid of claim 6, wherein the bars are bonded to the mounting plate.

8. The hearing aid of claim 6, wherein the bars are angle brackets.

9. The hearing aid of claim 7, wherein the outer mounting plate rim is milled off the mounting plate.

* * * * *